United States Patent
Graham et al.

(10) Patent No.: US 6,391,001 B1
(45) Date of Patent: May 21, 2002

(54) INTRAVENOUS LINE FLUSHING DEVICE

(76) Inventors: Jolie Graham; Joyce R. Varhola, both of 2275 Surrey Meadows, Henderson, NV (US) 89052

( * ) Notice: Subject to any disclaimer, the term of this patent is extended or adjusted under 35 U.S.C. 154(b) by 117 days.

(21) Appl. No.: 09/666,927

(22) Filed: Sep. 21, 2000

(51) Int. Cl.$^7$ ................................................. A61M 5/14
(52) U.S. Cl. .................... 604/82; 604/131; 128/DIG. 12
(58) Field of Search ............................. 604/82, 83, 90, 604/91, 131; 128/DIG. 12, DIG. 6

(56) References Cited

U.S. PATENT DOCUMENTS

| | | | |
|---|---|---|---|
| 4,447,230 A | | 5/1984 | Gula et al. |
| 4,507,116 A | * | 3/1985 | Leibinsohn ................... 604/142 |
| 4,935,009 A | | 6/1990 | Caldwell et al. |
| 5,242,392 A | | 9/1993 | Vaughn |
| 5,308,334 A | | 5/1994 | Sancoff |
| 5,318,520 A | | 6/1994 | Nakao |
| 5,356,375 A | | 10/1994 | Higley |
| 5,368,570 A | * | 11/1994 | Thompson et al. .......... 604/131 |
| 5,578,005 A | * | 11/1996 | Sancoff et al. ................ 604/82 |
| 5,720,728 A | * | 2/1998 | Ford ............................ 604/131 |
| 5,743,878 A | * | 4/1998 | Ross et al. ................... 604/131 |
| 5,776,105 A | * | 7/1998 | Corn ............................ 604/174 |
| 5,954,696 A | * | 9/1999 | Ryan ............................ 604/141 |

* cited by examiner

Primary Examiner—Denise L. Esquivel
Assistant Examiner—Marc Norman

(57) ABSTRACT

An intravenous line flushing device for preventing clotting of blood by the addition of saline solution to an intravenous line. The intravenous line flushing device includes a sleeve having an inner panel and an outer panel. Each of the panels has a top edge and a bottom edge. The top edge of the inner panel is integrally coupled to the top edge of the outer panel, and the bottom edge of the inner panel is integrally coupled to the bottom edge of the outer panel such that a space is defined between the inner and outer panels. The inner and outer panels are substantially air impermeable. A generally sealed container is positioned in the space between the inner and outer panels. A first agent is disposed in the space. A second agent is disposed in the container. Breaking the container mixes the first and second agents such that a gas is produced, which inflates the sleeve. A primary tube has a first end and a second end. The first end is adapted to removably fluidly engage a pouch. A secondary tube has a first end and a second end. The first end is fluidly coupled to the primary tube and positioned generally between the first and second ends of the primary tube. The second end of the secondary tube comprises a primary infusion port. The pouch contains a solution. The pouch is placed in the sleeve such that inflation of the sleeve forces the solution into the primary tube.

6 Claims, 2 Drawing Sheets

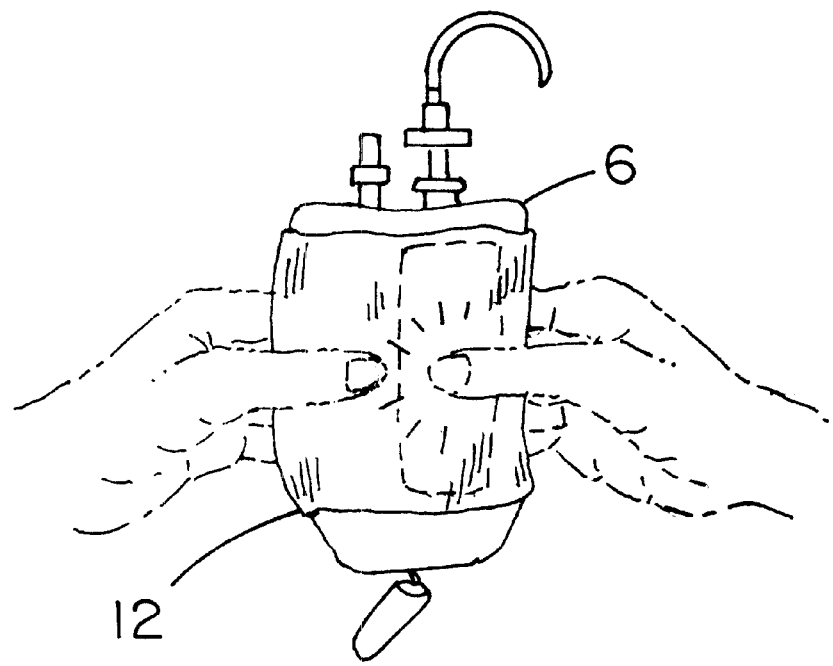
FIG. 2
FIG. 3
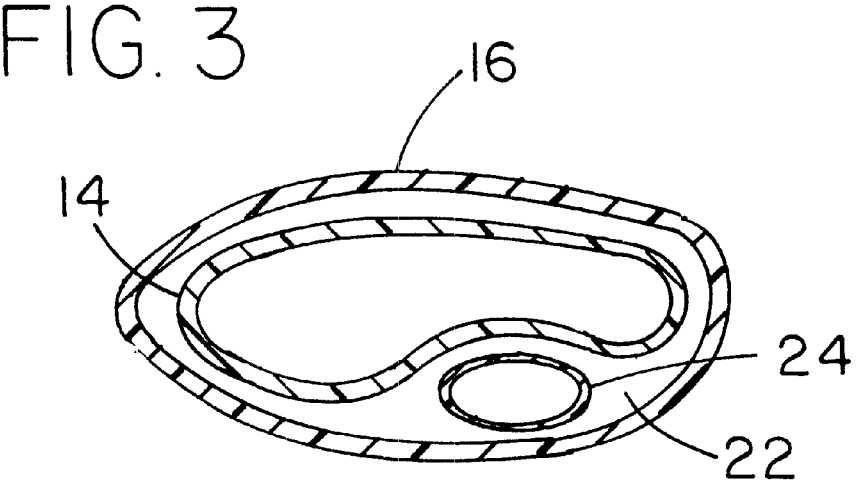

INTRAVENOUS LINE FLUSHING DEVICE

BACKGROUND OF THE INVENTION

1. Field of the Invention

The present invention relates to intravenous line devices and more particularly pertains to a new intravenous line flushing device for preventing clotting of blood by the addition of saline solution to an intravenous line.

2. Description of the Prior Art

The use of intravenous line devices is known in the prior art. More specifically, intravenous line devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,935,009; U.S. Pat. No. 5,356,375; U.S. Pat. No. 5,242,392; U.S. Pat. No. 5,308,334; U.S. Pat. No. 4,447,230; and U.S. Pat. No. 5,318,520.

While these devices fulfill their respective, particular objectives and requirements, the aforementioned patents do not disclose a new intravenous line flushing device. The inventive device includes a sleeve. The sleeve comprises an inner panel and an outer panel. Each of the panels has a top edge and a bottom edge. The top edge of the inner panel is integrally coupled to the top edge of the outer panel, and the bottom edge of the inner panel is integrally coupled to the bottom edge of the outer panel such that a space is defined between the inner and outer panels. The inner and outer panels are substantially air impermeable. A generally sealed container is positioned in the space between the inner and outer panels. A first agent is disposed in the space. A second agent is disposed in the container. Breaking the container mixes the first and second agents such that a gas is produced, which inflates the sleeve. A primary tube has a first end and a second end. The first end is adapted to removably fluidly engage a pouch. A secondary tube has a first end and a second end. The first end is fluidly coupled to the primary tube and positioned generally between the first and second ends of the primary tube. The second end of the secondary tube comprises a primary infusion port. The pouch contains a solution. The pouch is placed in the sleeve such that inflation of the sleeve forces the solution into the primary tube.

In these respects, the intravenous line flushing device according to the present invention substantially departs from the conventional concepts and designs of the prior art, and in so doing provides an apparatus primarily developed for the purpose of preventing clotting of blood by the addition of saline solution to an intravenous line.

SUMMARY OF THE INVENTION

In view of the foregoing disadvantages inherent in the known types of intravenous line devices now present in the prior art, the present invention provides a new intravenous line flushing device construction wherein the same can be utilized for preventing clotting of blood by the addition of saline solution to an intravenous line.

The general purpose of the present invention, which will be described subsequently in greater detail, is to provide a new intravenous line flushing device apparatus and method which has many of the advantages of the intravenous line devices mentioned heretofore and many novel features that result in a new intravenous line flushing device which is not anticipated, rendered obvious, suggested, or even implied by any of the prior art intravenous line devices, either alone or in any combination thereof.

To attain this, the present invention generally comprises a sleeve. The sleeve comprises an inner panel and an outer panel. Each of the panels has a top edge and a bottom edge. The top edge of the inner panel is integrally coupled to the top edge of the outer panel, and the bottom edge of the inner panel is integrally coupled to the bottom edge of the outer panel such that a space is defined between the inner and outer panels. The inner and outer panels are substantially air impermeable. A generally sealed container is positioned in the space between the inner and outer panels. A first agent is disposed in the space. A second agent is disposed in the container. Breaking the container mixes the first and second agents such that a gas is produced, which inflates the sleeve. A primary tube has a first end and a second end. The first end is adapted to removably fluidly engage a pouch. A secondary tube has a first end and a second end. The first end is fluidly coupled to the primary tube and positioned generally between the first and second ends of the primary tube. The second end of the secondary tube comprises a primary infusion port. The pouch contains a solution. The pouch is placed in the sleeve such that inflation of the sleeve forces the solution into the primary tube.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new intravenous line flushing device apparatus and method which has many of the advantages of the intravenous line devices mentioned heretofore and many novel features that result in a new intravenous line flushing device which is not anticipated, rendered obvious, suggested, or even implied by any of the prior art intravenous line devices, either alone or in any combination thereof.

It is another object of the present invention to provide a new intravenous line flushing device which may be easily and efficiently manufactured and marketed.

It is a further object of the present invention to provide a new intravenous line flushing device which is of a durable and reliable construction.

An even further object of the present invention is to provide a new intravenous line flushing device which is susceptible of a low cost of manufacture with regard to both materials and labor, and which accordingly is then susceptible of low prices of sale to the consuming public, thereby making such intravenous line flushing device economically available to the buying public.

Still yet another object of the present invention is to provide a new intravenous line flushing device which provides in the apparatuses and methods of the prior art some of the advantages thereof, while simultaneously overcoming some of the disadvantages normally associated therewith.

Still another object of the present invention is to provide a new intravenous line flushing device for preventing clotting of blood by the addition of saline solution to an intravenous line.

Yet another object of the present invention is to provide a new intravenous line flushing device which includes a sleeve. The sleeve comprises an inner panel and an outer panel. Each of the panels has a top edge and a bottom edge. The top edge of the inner panel is integrally coupled to the top edge of the outer panel, and the bottom edge of the inner panel is integrally coupled to the bottom edge of the outer panel such that a space is defined between the inner and outer panels. The inner and outer panels are substantially air impermeable. A generally sealed container is positioned in the space between the inner and outer panels. A first agent is disposed in the space. A second agent is disposed in the container. Breaking the container mixes the first and second agents such that a gas is produced, which inflates the sleeve. A primary tube has a first end and a second end. The first end is adapted to removably fluidly engage a pouch. A secondary tube has a first end and a second end. The first end is fluidly coupled to the primary tube and positioned generally between the first and second ends of the primary tube. The second end of the secondary tube comprises a primary infusion port. The pouch contains a solution. The pouch is placed in the sleeve such that inflation of the sleeve forces the solution into the primary tube.

Still yet another object of the present invention is to provide a new intravenous line flushing device that adds a controlled and filtered amount of saline solution to an intravenous line. Saline solution helps to prevent blood clotting around the entering point of an intravenous line so that the patient need not have the intravenous line removed and replaced in a different location.

Even still another object of the present invention is to provide a new intravenous line flushing device that allows the user to wear the saline pouch on their body because the pressure of the sleeve prevents the requirement that the pouch be hung.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a schematic front view of the present invention.

FIG. 3 is a schematic cross-sectional view taken along line 3—3 of the present invention.

DESCRIPTION OF THE PREFERRED EMBODIMENT

Figure 1:
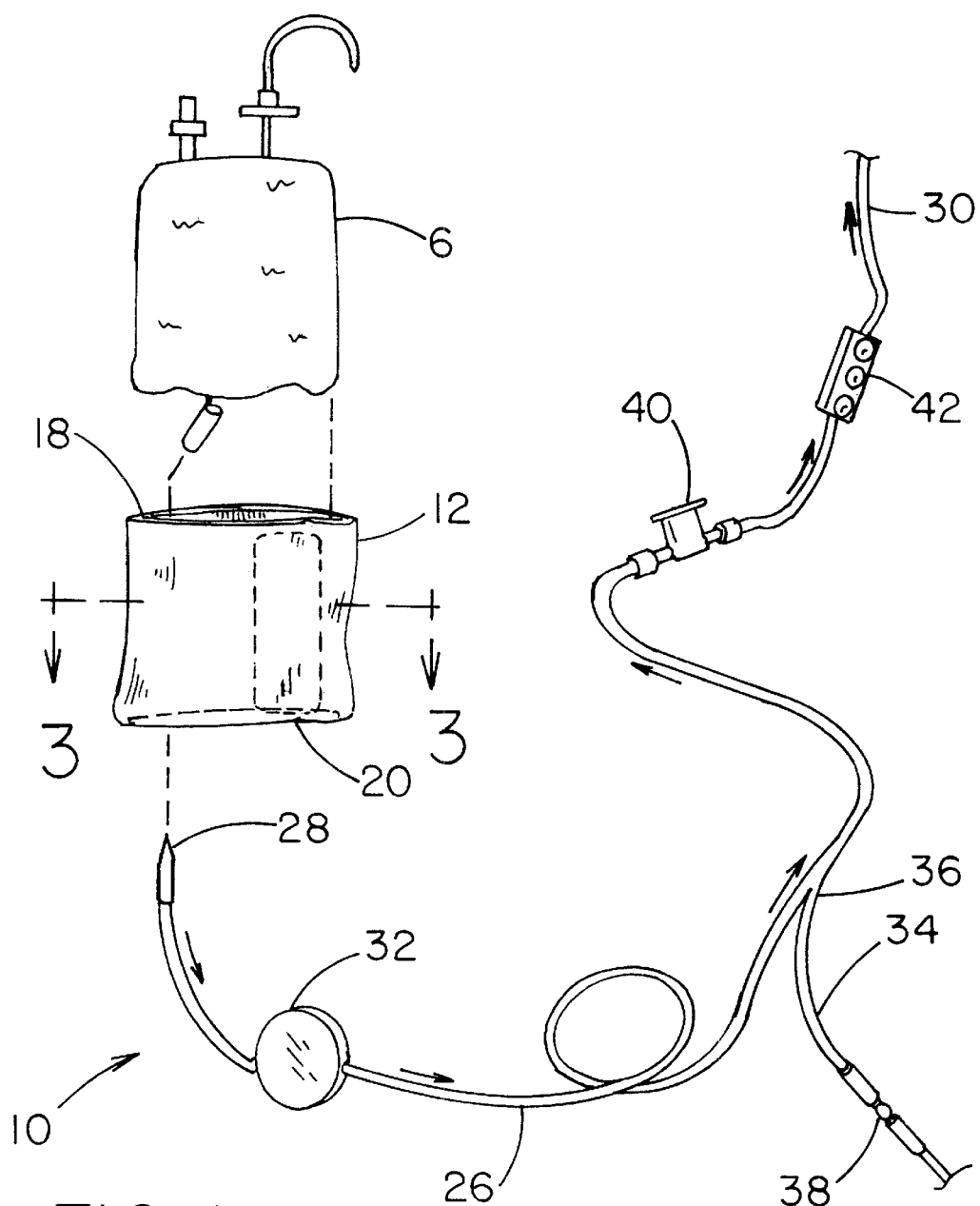
FIG. 1 is a schematic front perspective view of a new intravenous line flushing device according to the present invention.

With reference now to the drawings, and in particular to FIGS. 1 through 3 thereof, a new intravenous line flushing device embodying the principles and concepts of the present invention and generally designated by the reference numeral 10 will be described.

As best illustrated in FIGS. 1 through 3, the intravenous line flushing device 10 generally comprises a sleeve 12. The sleeve 12 comprises an inner panel 14 and an outer panel 16. Each of the panels has a top edge 18 and a bottom edge 20. The top edge 18 of the inner panel 14 is integrally coupled to the top edge 18 of the outer panel 16. The bottom edge 20 of the inner panel 14 is integrally coupled to the bottom edge 20 of the outer panel 18 such that a space 22 is defined between the inner and outer panels. The inner and outer panels are generally both sleeves which are coupled together. The inner 14 and outer 16 panels are substantially air impermeable. The inner 14 and outer 16 panels are comprised of a resiliently flexible material which is preferably an elastomeric material or a plastic.

A container 24 is positioned in the space 22 between the inner and outer panels. The container 24 is generally sealed. The container is generally frangible.

A first agent is disposed in the space 22. The first agent preferably comprises bicarbonate. A second agent is disposed in the container 24. The second agent preferably comprises an acid. Breaking the container 24 by applying pressure to it mixes the first and second agents such that a gas is produced. The gas inflates the sleeve 12.

A primary tube 26 has a first end 28 and a second end 30. The first end 28 is adapted to removably and fluidly engage a pouch 6 containing saline solution such that the saline solution may enter the primary tube 26. The primary tube 26 may be used as the intravenous line itself, or it may be fluidly coupled to another line used as the intravenous line.

A filter means 32 filters bacteria and air out of the saline solution and preferably controls flow rate of the solution through the primary tube 26. The filter means 32 is fluidly coupled to the primary tube 26 and positioned between the first and second ends of the primary tube such that the saline solution travels through the filter means. The filter means 32 ideally filters generally 1 cc of saline solution per hour.

A secondary tube 34 has a first end 36 and a second end 38. The first end 36 is fluidly coupled to the primary tube 26 and positioned generally between the filter means 32 and the second end 30 of the primary tube 26. The second end 38 of the secondary tube comprises an primary infusion port.

A conventional priming means 40 for priming the primary tube is fluidly coupled to the primary tube 26 and positioned between the secondary tube 34 and the second end 30 of the primary tube 26.

A plurality of secondary infusion ports 42 is fluidly coupled to the primary tube 26 and positioned between the priming means 40 and the second end 30 of the primary tube 26.

In use, a pouch 6, preferably containing saline solution, is placed in the sleeve 12 and fluidly coupled to the first end 28 of the primary tube 26. The container 24 is broken so that the agents mix to produce a gas and inflate the sleeve 12. The inflation of the sleeve applies pressure on the pouch 6 so that the solution is forced out of the pouch and into the primary tube 26. The filter means 32 is a conventional filter that filters any bacteria or air out of the solution. The filter means 32 also regulates the volume of the solution which may travel through the primary tube. The additional infusion ports 38, 42 are used so that other fluids may be added to the line. Also envisioned are uses of the sleeve 12 for general fluids whose flow may be regulated by the filter means 32. The sleeve 12 allows the forced entry of fluids into an intravenous line without the need for the pouch 6 to be hung.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. An intravenous line flushing device for forcing saline solution through an intravenous line, the saline solution being located in a pouch having generally flexible walls, said device comprising:

a sleeve, said sleeve comprising an inner panel and an outer panel, each of said panels having a top edge and a bottom edge, said top edge of said inner panel being integrally coupled to said top edge of said outer panel, said bottom edge of said inner panel being integrally coupled to said bottom edge of said outer panel such that a space is defined between said inner and outer panels, said inner and outer panels being substantially air impermeable, said inner and outer panels comprising a resiliently flexible material;

a container, said container being positioned in said space between said inner and outer panels, said container being generally sealed, said container being generally frangible;

a first agent, said first agent being disposed in said space;

a second agent, said second agent being disposed in said container;

wherein breaking said container mixes said first and second agents such that a gas is produced, said gas inflating said sleeve;

a primary tube, said primary tube having a first end and a second end, said first end being adapted to removably fluidly engage said pouch;

a secondary tube, said secondary tube having a first end and a second end, said first end being fluidly coupled to said primary tube and positioned generally between said first and second ends of said primary tube, said second end of said secondary tube comprising an primary infusion port.

2. The intravenous line flushing device as in claim 1, further comprising:

a filter means for filtering bacteria and air out of said saline solution, said filter means being fluidly coupled to said primary tube and positioned between said first end of said primary tube and said secondary tube such that said saline solution travels through said filter means.

3. The intravenous line flushing device as in claim 1, further comprising:

a priming means for priming said primary tube, said priming means being fluidly coupled to said primary tube and positioned between said secondary tube and said second end of said primary tube.

4. The intravenous line flushing device as in claim 1, further comprising:

a plurality of secondary infusion ports, said secondary infusion ports being fluidly coupled to said primary tube and positioned between said secondary tube and said second end of said primary tube.

5. An intravenous line flushing device for forcing solution through an intravenous line, the solution being located in a pouch having generally flexible walls, said device comprising:

a sleeve, said sleeve comprising an inner panel and an outer panel, each of said panels having a top edge and a bottom edge, said top edge of said inner panel being integrally coupled to said top edge of said outer panel, said bottom edge of said inner panel being integrally coupled to said bottom edge of said outer panel such that a space is defined between said inner and outer panels, said inner and outer panels being substantially air impermeable, said inner and outer panels comprising a resiliently flexible material;

a container, said container being positioned in said space between said inner and outer panels, said container being generally sealed, said container being generally frangible;

a first agent, said first agent being disposed in said space;

a second agent, said second agent being disposed in said container;

wherein breaking said container mixes said first and second agents such that a gas is produced, said gas inflating said sleeve;

a primary tube, said primary tube having a first end and a second end, said first end being adapted to removably fluidly engage said pouch such that the solution may enter said primary tube;

a filter means for filtering bacteria and air out of said solution and adapted for controlling flow rate of said solution through said primary tube, said filter means being fluidly coupled to said primary tube and positioned between said first and second ends of said primary tube such that said solution travels through said filter means.

6. An intravenous line flushing device for forcing saline solution through an intravenous line, the saline solution being located in a pouch having generally flexible walls, said device comprising:

a sleeve, said sleeve comprising an inner panel and an outer panel, each of said panels having a top edge and a bottom edge, said top edge of said inner panel being integrally coupled to said top edge of said outer panel, said bottom edge of said inner panel being integrally coupled to said bottom edge of said outer panel such that a space is defined between said inner and outer panels, said inner and outer panels being substantially air impermeable, said inner and outer panels comprising a resiliently flexible material;

a container, said container being positioned in said space between said inner and outer panels, said container being generally sealed, said container being generally frangible;

a first agent, said first agent being disposed in said space, said first agent comprising a bicarbonate;

a second agent, said second agent being disposed in said container, said second agent comprising an acid;

wherein breaking said container mixes said first and second agents such that a gas is produced, said gas inflating said sleeve;

a primary tube, said primary tube having a first end and a second end, said first end being adapted to removably fluidly engage said pouch such that the saline solution may enter said primary tube;

a filter means for filtering bacteria and air out of said saline solution, said filter means being fluidly coupled to said primary tube and positioned between said first and second ends of said primary tube such that said saline solution travels through said filter means, said filter means being adapted for filtering generally 1 cc of saline solution per hour;

a secondary tube, said secondary tube having a first end and a second end, said first end being fluidly coupled to said primary tube and positioned generally between said filter means and said second end of said primary tube, said second end of said secondary tube comprising an primary infusion port;

a priming means for priming said primary tube, said priming means being fluidly coupled to said primary tube and positioned between said secondary tube and said second end of said primary tube; and a plurality of secondary infusion ports, said secondary infusion ports being fluidly coupled to said primary tube and positioned between said priming means and said second end of said primary tube.

* * * * *